US011707623B2

(12) United States Patent
Golan et al.

(10) Patent No.: US 11,707,623 B2
(45) Date of Patent: Jul. 25, 2023

(54) SURGICAL IMPLANT SYSTEM

(71) Applicant: NYXOAH S.A., Mont-Saint-Guibert (BE)

(72) Inventors: Shiran Golan, Mount-Saint-Guibert (BE); Guy Siman, Mount-Saint-Guibert (BE); Yoel Ben Yosef, Mount-Saint-Guibert (BE); Ronen Adimor, Mount-Saint-Guibert (BE); Roi Moshe Tsukran, Mount-Saint-Guibert (BE)

(73) Assignee: Nyxoah S.A., Mont-Saint-Guibert (BE)

(*) Notice: Subject to any disclaimer, the term of this patent is extended or adjusted under 35 U.S.C. 154(b) by 0 days.

(21) Appl. No.: 16/488,141

(22) PCT Filed: Feb. 28, 2018

(86) PCT No.: PCT/EP2018/054913
§ 371 (c)(1),
(2) Date: Aug. 22, 2019

(87) PCT Pub. No.: WO2018/158305
PCT Pub. Date: Sep. 7, 2018

(65) Prior Publication Data
US 2020/0001082 A1 Jan. 2, 2020

Related U.S. Application Data

(60) Provisional application No. 62/464,917, filed on Feb. 28, 2017.

(51) Int. Cl.
*A61N 1/36* (2006.01)
*A61N 1/05* (2006.01)
(52) U.S. Cl.
CPC .......... *A61N 1/3611* (2013.01); *A61N 1/3601* (2013.01); *A61N 1/0548* (2013.01)

(58) Field of Classification Search
CPC .... A61N 1/3611; A61N 1/3601; A61N 1/375; A61N 1/0548
See application file for complete search history.

(56) References Cited

U.S. PATENT DOCUMENTS 2,125,008 A 7/1938 Scholl
4,370,984 A 2/1983 Cartmell
(Continued)

FOREIGN PATENT DOCUMENTS

CN 106422063 A 2/2017
JP 09234189 A 9/1997
(Continued)

OTHER PUBLICATIONS

International Search Report and Written Opinion from International Application No. PCT/EP2018/054913 dated Jun. 12, 2018.
(Continued)

*Primary Examiner* — Alyssa M Alter
(74) *Attorney, Agent, or Firm* — Dorsey & Whitney LLP

(57) ABSTRACT

The disclosed subject matter is directed to a surgical implant and a device for its activation. The surgical implant comprises a substantially planar central body portion having a top side and a bottom side and at least two adjustable wing portions. In addition, the implant comprises at least two connecting members, each one of the at least two connecting members extending from opposite sides of the central body portion, the each one of the at least two connecting members being configured for flexibly connecting each one of the at least two wing portions at opposite sides to said central body portion.

19 Claims, 13 Drawing Sheets

(56) References Cited

U.S. PATENT DOCUMENTS

| | | | |
|---|---|---|---|
| D272,943 S | 3/1984 | Stone et al. | |
| 4,856,499 A | 8/1989 | Kelly | |
| 5,261,400 A * | 11/1993 | Bardy | A61N 1/3918 607/5 |
| D349,958 S | 8/1994 | Peterson et al. | |
| 5,511,548 A | 4/1996 | Riazzi et al. | |
| 5,538,500 A | 7/1996 | Peterson | |
| D372,787 S | 8/1996 | Dozier et al. | |
| 5,645,586 A * | 7/1997 | Meltzer | A61N 1/3956 220/4.23 |
| 5,995,874 A | 11/1999 | Borza | |
| 6,031,746 A | 2/2000 | Steigerwald et al. | |
| D454,955 S | 3/2002 | Dunshee et al. | |
| D477,085 S | 7/2003 | Sanfilippo | |
| D539,424 S | 3/2007 | Persson et al. | |
| 7,381,859 B2 | 6/2008 | Hunt et al. | |
| D610,677 S | 2/2010 | Tyce | |
| 7,772,582 B2 | 8/2010 | Chen et al. | |
| 7,945,334 B2 * | 5/2011 | Jimenez | A61N 1/3787 607/61 |
| 7,976,519 B2 | 7/2011 | Bubb et al. | |
| D655,807 S | 3/2012 | Mogensen et al. | |
| 8,149,064 B2 | 4/2012 | Paul et al. | |
| D683,851 S | 6/2013 | Greenhalgh | |
| 8,577,465 B2 | 11/2013 | Mashiach | |
| D715,928 S | 10/2014 | Kyvik et al. | |
| D735,322 S | 7/2015 | Tyce et al. | |
| D755,980 S | 5/2016 | Jakobsen et al. | |
| D756,513 S | 5/2016 | Cheney | |
| D759,828 S | 6/2016 | Riedle | |
| D764,657 S | 8/2016 | Bokelman et al. | |
| 9,504,839 B2 | 11/2016 | Leven | |
| D773,665 S | 12/2016 | Cheney et al. | |
| D773,666 S | 12/2016 | Cheney et al. | |
| D777,329 S | 1/2017 | Montoya et al. | |
| D778,451 S | 2/2017 | Takizawa et al. | |
| D780,311 S | 2/2017 | Cheney et al. | |
| D790,714 S | 6/2017 | Addison | |
| 9,818,530 B2 | 11/2017 | Muratov et al. | |
| 9,935,498 B2 | 4/2018 | Joshi | |
| D819,202 S | 5/2018 | Svantesson et al. | |
| 9,962,500 B2 | 5/2018 | Holtwick et al. | |
| RE47,100 E | 10/2018 | Smith et al. | |
| D866,769 S | 11/2019 | Yosef et al. | |
| 2002/0077599 A1 | 6/2002 | Wojcik | |
| 2003/0040291 A1 | 2/2003 | Brewer | |
| 2004/0010233 A1 | 1/2004 | Hjertman et al. | |
| 2005/0068019 A1 | 3/2005 | Nakamura et al. | |
| 2007/0156180 A1 * | 7/2007 | Jaax | A61N 1/32 607/2 |
| 2009/0230777 A1 | 9/2009 | Baarman et al. | |
| 2010/0259109 A1 | 10/2010 | Sato | |
| 2010/0268313 A1 | 10/2010 | Conn | |
| 2011/0257659 A1 * | 10/2011 | Mehdizadeh | A61N 1/0551 606/129 |
| 2012/0089081 A1 | 4/2012 | Chao et al. | |
| 2012/0212074 A1 | 8/2012 | Uchida | |
| 2012/0235504 A1 | 9/2012 | Kesler et al. | |
| 2013/0085560 A1 | 4/2013 | Mashiach | |
| 2013/0200716 A1 | 8/2013 | Kesler et al. | |
| 2013/0278071 A1 | 10/2013 | Komiyama | |
| 2014/0003189 A1 | 1/2014 | Gerl et al. | |
| 2014/0031890 A1 | 1/2014 | Mashiach et al. | |
| 2014/0097791 A1 | 4/2014 | Lisuwandi | |
| 2014/0225449 A1 | 8/2014 | Kurs | |
| 2014/0339910 A1 | 11/2014 | Sealy et al. | |
| 2014/0358026 A1 | 12/2014 | Mashiach et al. | |
| 2014/0358197 A1 | 12/2014 | Mashiach et al. | |
| 2014/0371802 A1 | 12/2014 | Mashiach et al. | |
| 2015/0108945 A1 | 4/2015 | Yan et al. | |
| 2015/0171793 A1 | 6/2015 | Regier | |
| 2015/0270719 A1 | 9/2015 | Kurs et al. | |
| 2015/0290455 A1 | 10/2015 | Bornzin et al. | |
| 2015/0343221 A1 | 12/2015 | Mashiach | |
| 2016/0067106 A1 | 3/2016 | Howell et al. | |
| 2016/0067477 A1 * | 3/2016 | Dubuclet | A61N 1/0553 607/117 |
| 2017/0007442 A1 | 1/2017 | Dietz | |
| 2018/0200520 A1 | 7/2018 | Tranchina et al. | |

FOREIGN PATENT DOCUMENTS

| | | |
|---|---|---|
| WO | 2009051539 A1 | 4/2009 |
| WO | 2009091267 A2 | 7/2009 |
| WO | 2010059097 A1 | 5/2010 |
| WO | 2011008165 A1 | 1/2011 |
| WO | 2012148474 A1 | 11/2012 |
| WO | 2013164831 A1 | 11/2013 |

OTHER PUBLICATIONS

U.S. Appl. No. 62/464,917, filed Feb. 28, 2017.
Direct Home Medical. Link: https://www.directhomemedical.com/cart/merchant.mvc?Screen=PROD&Product_Code=z1-travel-cpap-powershell-module-hdmusa&Store_Code=D H M&gclid=EAlalQobChMlkea7sdvj3gIV9fjBx2jLQa5EAQYBSABEglckfD_BwE, visited Nov. 20, 2018. PowerShell Z1 Series CPAP Machines. (Year: 2018).
Final Office Action for U.S. Appl. No. 15/533,089 dated May 3, 2019.
International Search Report and Written Opinion from International Application No. PCT/EP2015/078104 dated Aug. 22, 2016.
Issue Notification for U.S. Appl. No. 29/591,095 dated Feb. 5, 2020.
Issue Notification for U.S. Appl. No. 29/596,273 dated Oct. 23, 2019.
Non-Final Office Action for U.S. Appl. No. 15/533,089 dated Dec. 2, 2019.
Non-Final Office Action for U.S. Appl. No. 15/533,089 dated Oct. 26, 2018.
Notice of Allowance for U.S. Appl. No. 29/591,095 dated Jul. 5, 2019.
Notice of Allowance for U.S. Appl. No. 29/591,095 dated Oct. 23, 2019.
Restriction Requirement for U.S. Appl. No. 15/533,089 dated Aug. 10, 2018.
Restriction Requirement for U.S. Appl. No. 29/591,095 dated Apr. 22, 2019.
U.S. Appl. No. 15/533,089, filed Dec. 21, 2017.
U.S. Appl. No. 29/591,095, filed Jan. 17, 2017.
U.S. Appl. No. 29/610,459, filed Jul. 12, 2017.
Ping, et al., "A Frequency Control Method for Regulating Wireless Power to Implantable Devices", IEEE Transactions on Biomedical Circuits and Systems, vol. 2, No. 1, Mar. 1, 2008.
Advisory Action for U.S. Appl. No. 15/533,089 dated Sep. 14, 2020.
Final Office Action for U.S. Appl. No. 15/533,089 dated Apr. 13, 2021.
Final Office Action for U.S. Appl. No. 15/533,089 dated Jun. 8, 2020.
Issue Notification for U.S. Appl. No. 29/721,611 dated Mar. 17, 2021.
Non-Final Office Action for U.S. Appl. No. 15/533,089 dated Dec. 8, 2020.
Notice of Allowance for U.S. Appl. No. 29/721,611 dated Apr. 16, 2020.
Notice of Allowance for U.S. Appl. No. 29/721,611 dated Jul. 30, 2020.
Kiri, et al., "Class D and Class E Selectable Power Amplifier", IEEE INTELEC—31st International Telecommunications Energy Conference, Dept. of Electronics Engineering and Computer Science,Fukuoka University Japan, 2009, 4.
Non-Final Office Action for U.S. Appl. No. 29/706,981 dated Feb. 23, 2022.
"A Review of Genio System from Nyxoah", by Veik Veer—ENT Surgeon, on YouTube Jul. 25, 2020, Jul. 2020, 1 page.
Ex Parte Quayle Action for U.S. Appl. No. 29/706,981 mailed Sep. 20, 2022.

(56) References Cited

OTHER PUBLICATIONS

Communication Pursuant to Article 94(3) EPC for European Patent Application No. 18714702.0 dated May 10, 2023.

\* cited by examiner

SURGICAL IMPLANT SYSTEM

TECHNOLOGICAL FIELD

The disclosed subject matter is directed to a surgical implant system, device and methods related to medical conditions such as the obstructive sleep apnea. In particular, the disclosed subject matter is directed to an implant for neurostimulation and associated activation devices and methods.

BACKGROUND

Various types of neurostimulators are known in the art. In the field of neurostimulators for the stimulation of the hypoglossal nerves, the following provide some examples, details of which are incorporated herein by reference.

U.S. Pat. No. 8,577,465 describes an implant unit that may include a flexible carrier, at least one pair of modulation electrodes on the flexible carrier, and at least one implantable circuit in electrical communication with the at least one pair of modulation electrodes. The at least one pair of modulation electrodes and the at least one circuit may be configured for implantation through derma on an underside of a subject's chin and for location proximate to terminal fibers of the medial branch of the subject's hypoglossal nerve, such that an electric field extending from the at least one pair of modulation electrodes can modulate one or more of the terminal fibers of the medial branch of the hypoglossal nerve.

US2013085560 describes an implant unit configured for implantation into a body of a subject and may include an antenna configured to receive a signal. The implant unit may also include at least one pair of modulation electrodes configured to be implanted into the body of the subject in the vicinity of at least one nerve to be modulated, the at least one pair of modulation electrodes being configured to receive an applied electric signal in response to the signal received by the antenna and generate an electrical field to modulate the at least one nerve from a position where the at least one pair of modulation electrodes does not contact the at least one nerve.

The following provides for an example of an activation tool used to active a neurostimulator during the surgical procedure. US201403189 disclosure of which is incorporated herein by reference, describes an implant unit delivery tool having an implant tool and an implant activator. The implant tool may be configured to retain an implant unit during an implantation procedure in which the implant unit is fixated to tissue. The implant activator may be associated with the implant tool. Additionally, the implant activator may be configured to selectively transfer power to the implant unit during the implantation procedure to cause modulation of at least one nerve in the body of a subject prior to final fixation of the implant unit to the tissue.

General Description

In one aspect of the disclosed subject matter, there is disclosed a surgical implant. The surgical implant in accordance with this aspect comprises:
- a substantially planar central body portion having a top side and a bottom side;
- at least two adjustable wing portions;
- at least two connecting members, each one of the at least two connecting members extending from opposite sides of the central body portion, the each one of the at least two connecting members being configured for flexibly connecting each one of the at least two wing portions at opposite sides to said central body portion.

Any one of the following embodiments may apply to any one of the aspects of the disclosed subject matter, alone or in combination:
- the central body may have one side substantially planar and an opposite side having at least a partially arched surface.
- the wings may be more flexible than the central body portion.
- the wings and the central body portion may be made from the same material.
- the wings and the central body portion may be made from different materials.
- the flexible connection is via a hinge and the hinge portion is thinner than an adjacent portion of the wing of which it is a part.
- each one of said at least two connecting members extend from the central body through at least one hinge member.
- each one of said at least two connecting members extend from the central body through at least one hinge member and wherein each one of said at least two wing portions being hingedly articulated to the at least one hinge through an extension member extending between the central body portion and the at least one of the at least two wing portions.
- the connecting member may be a flexible element configured to deform in at least one direction.
- the flexible element may be in the form of a flexible arch permitting bending movement along its length in a first direction such that the central body and each of the at least two wing portions flex away from each other.
- Further may comprise a flexible arch comprising:
- at least one central segment arranged along the length of the flexible arch; and
- at least two hinge structures, each one of the hinge structures being disposed between the central body and the at least one central segment and the one of the at least two wing portions and the central segment and oriented in a direction transverse to the length of the central segment.
- the flexible arch may be formed from a unitary elastomeric material and the hinges comprise living hinges.
- the flexible arch may be formed from multiple segments; the multiple segments may be connected through living hinges; the multiple segments may be connected through material, the material may have a thickness less than the thickness of the segments.
- the flexible arch may have a narrowing width, having the largest width at the area of connection to the central body and a narrower width at the area of connection with at least one of the wing portions.
- the flexible arch may have a non-uniform thickness and/or a non-uniform width.
- the surgical implant may be formed from a unitary elastomeric material.
- the surgical implant may comprise at least one anchoring arrangement.
- the surgical implant may comprise at least one anchoring arrangement, wherein the anchoring arrangement may be in a form of at least one suture hole.
- the surgical implant may comprise at least one anchoring arrangement, wherein the anchoring arrangement may be in a form of at least one suture hole, wherein the at least one suture hole is provided on the central body portion and/or the at least one of the at least two wing portions.

the anchoring arrangement may be in the form of a suture hole, the suture hole may be reinforced internally and/or externally.

the reinforced anchoring arrangement may comprise an embedded reinforcing element.

the reinforced anchoring arrangement may comprise an embedded reinforcing element and/or a reinforcing layer of material forming part of the arrangement.

the reinforcing anchoring arrangement may be a mesh material.

the anchoring arrangement may be part of the load bearing reinforcing element of the implant;

the surgical implant may comprise at least one anchoring arrangement, wherein the anchoring arrangement may be configured for anchoring the surgical implant at the implant location, anchoring at least said at least two wing portions opposite one from the other.

the anchoring arrangement is configured to prevent damage to at least a portion of the internal components of the surgical implant.

the implant unit may comprise an anchoring arrangement which may be chemical or mechanical; in some embodiments, the anchoring arrangement may comprise an adhesive. In another embodiment, the anchoring arrangement may comprise staples, sutures, absorbable sutures, a mechanical encapsulation of at least a portion of the implant unit within the body.

the at least two wing portions may have at least one degree of freedom and may be flexibly adjustable to various angular dispositions with respect to the main body.

the at least two wing portions may have at least one degree of freedom and may be flexibly adjustable to various angular dispositions with respect to the main body, and wherein the angular disposition may be between 0 to up to 270 degrees; in accordance with an embodiment, the angular disposition may be between −90 to up to 270 degrees.

the at least two wing portions may have at least one degree of freedom and may be flexibly adjustable to various angular dispositions along more than one axis and in some embodiments, along and/or around three axis.

the at least two wing portions have more than three degrees of freedom and may be flexibly adjustable to various angular dispositions with respect to the main body and/or the connecting members.

the flexible arch is formed from a unitary elastomeric material and the hinges comprise living hinges.

at least in one configuration of the implant device, the flexible arch may protrude beyond the top side of the substantially planar surface of the central body.

at least in one configuration of the implant device, the flexible arch may protrude at an angle beyond the planar surface of the top side of the central body.

at least the central body portion is further provided with internally disposed load bearing reinforcing structure, configured to provide structural rigidity to the central body portion.

at least the central body portion is further provided with internally disposed load bearing reinforcing structure, configured to provide structural rigidity to the central body portion; in one embodiment the reinforcing structure may be a system of elements; in another embodiment the reinforcing structure may be a unitary element.

the load bearing reinforcement structure may be formed from any suitable material configured to hold structural integrity under exhersion of force thereupon.

The load bearing reinforcement structure may be formed from any one of a polymer, polyether ether ketone (PEEK), ULTEM, liquid crystal polymer (LCP), ceramics, or alloy of compatible materials or combination of materials.

the implant may be substantially encapsulated at least in one layer of a biocompatible polymer including at least one of silicone, phenyltrimethoxysilane (PTMS), polymethyl methacrylate (PMMA), parylene C, polyimide, liquid polyimide, laminated polyimide, epoxy, polyether ether ketone (PEEK), liquid crystal polymer (LCP), KAPTON, or combinations thereof.

the implant may be encapsulated at least in one layer of a biocompatible polymer, and include one or more additional layer covering portions thereof.

the implant may be encapsulated at least in one layer of a biocompatible material, and may include ceramic material, thermoplastic material such as ULTEM, or other compatible materials.

the central body portion may be provided with an antenna configured to receive a signal and wherein each one of the at least two wing portions is provided with at least a pair of electrodes in electric communication with the antenna, the electrodes being configured to receive an electric current in response to the signal received by the antenna, such that at least one of pair of electrodes is configured to emit an electrical field.

the first pair of electrodes and the second pair of electrodes can be activated to simultaneously generate respective electric fields.

the first pair of electrodes and the second pair of electrodes may be partially covered at their periphery with the encapsulating material, having at least a portion thereof exposed.

the first pair of electrodes and the second pair of electrodes may be partially embedded within the encapsulating material and comprise an outer layer of encapsulating material extending thereover and leaving at least a portion thereof exposed to the environment.

the surgical implant is configured to conform to an exterior surface of a genioglossus muscle of a subject, such that the at least two wing portions are positioned at the sides of the genioglossus muscle adjacent to terminal fibers of a medial branch of a hypoglossal nerve, and wherein the electrodes generate electric field sufficient to modulate the terminal fibers of a medial branch, when spaced apart thereof.

at least one of the first pair of electrodes and the second pair of electrodes are connected to electric circuitry through wires.

at least one of the first pair of electrodes and the second pair of electrodes are connected to electric circuitry through wires, the circuitry being disposed on the central body and the wires being configured to extend through the respective connecting members.

the wires may be disposed such that the integrity of the communication between the electric circuitry and the electrodes is not impaired when at least one of the connecting members is displaced.

the wires may be coiled wires.

the wires may be undulating.

In another aspect of the disclosed subject matter there is disclosed an implant unit activation device, comprising: a main body comprising an implant activator and an axially displaceable adaptor configured to displace relative the main body, the implant activator having a power source and being configured to wirelessly transfer energy from the power source to an implant unit during implantation of the implant unit into the body of a subject to cause stimulation of at least one nerve in the body of the subject; and wherein the axial displacement of the adaptor allows adjusting of the amount of energy received by the implant unit.

The amount of energy may be adjusted directly through the implant unit activation device.

In yet another aspect, there is provided a method of positioning and activating a neurostimulation implant device, the method comprising:
providing a neurostimulation device having:
 a central body portion provided with a first antenna configured to receive a signal;
 at least a first pair of electrodes and a second pair of electrodes operatively coupled to a central body portion;
 wherein the central body portion is in electric communication with at least the first pair of electrodes and the second pair of electrodes, said at least first pair of electrodes and the second pair of electrodes being configured to receive an electric signal in response to the signal received by the first antenna, such that at least one of pair of electrodes is configured to emit an electrical field to stimulate a nerve in a subject's body,
providing an implant unit activation device, the device comprising: a main body comprising an implant activator having a power source, a second antenna configured to provide a signal to the first antenna and an axially displaceable adaptor/retractor associated with the implant activator, the implant activator configured to wirelessly transfer energy from a power source comprised therein to the neurostimulation device during implantation to cause stimulation of at least one nerve in the body of the subject; and
 wherein the axial displacement of the adaptor\retractor from at least a first position to at least a second position allows adjusting of the degree of energy received by the implant unit;
identifying the stimulation threshold by determining a degree of nerve stimulation response for each of the at least first pair of electrodes and a second pair of electrodes by positioning said first pair of electrodes at an estimated implant location proximal to the nerve and selectively displacing the second antenna by repositioning the main body with respect to the adaptor/retractor to deliver a first amount of current and a second amount of current required to obtain a stimulation threshold in at least the first pair of electrodes based on one or more patient signals;
positioning the at least the second pair of electrodes at an estimated location and delivering the second amount of power required and determining a degree of nerve stimulation by the at least said second pair of electrodes.

In one embodiment the implant may be configured for treatment of obstructive sleep apnea and the location of implantation may be in the vicinity of the hypoglossal nerve. In accordance with this embodiment the neurostimulation device may be configured to modulate at least one branch of the hypoglossal nerves.

The second amount may be greater or equal to the first amount of power.

The second amount may be equal to or less relative the first amount of power.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which.

DETAILED DESCRIPTION OF EMBODIMENTS

Figure 1A:
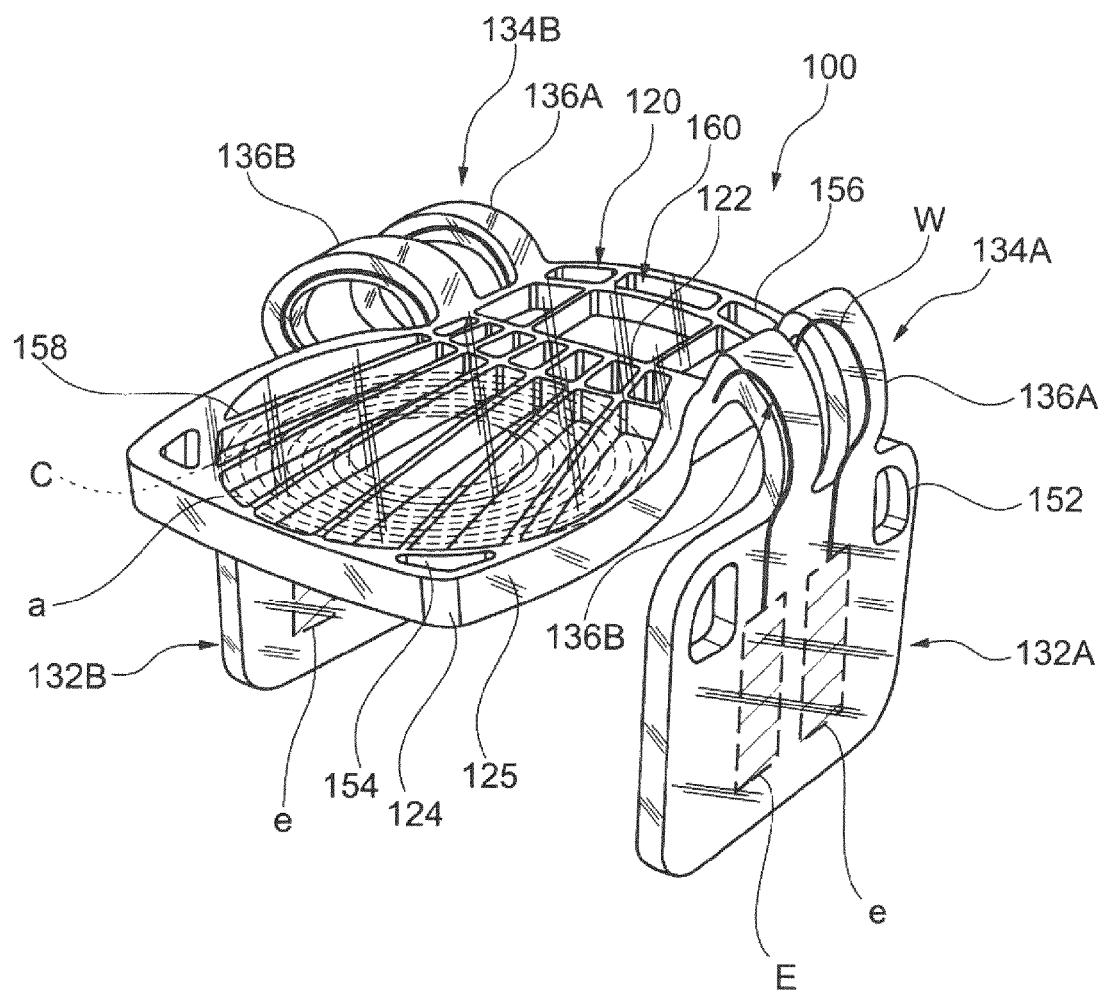
FIG. 1A is a perspective view of the surgical implant in accordance with one example of the disclosed subject matter.

Examples of the presently disclosed subject matter relate generally to a surgical implant configured for modulating a nerve through the delivery of energy. Nerve modulation, or neural modulation, includes inhibition (e.g. blockage), stimulation, modification, regulation, or therapeutic alteration of activity, electrical or chemical, in the central, peripheral, or autonomic nervous system. Nerve modulation may take the form of nerve stimulation, which may include providing energy to the nerve to create a voltage change sufficient for the nerve to activate, or propagate an electrical signal of its own. As referred to herein, modulation of a nerve may include modulation of an entire nerve and/or modulation of a portion of a nerve. In patients with obstructive sleep apnea (OSA), for example, a primary target response of nerve stimulation may include contraction of a tongue muscle in order to move the tongue to a position that does not block the patient's airway, the cause of obstruction in OSA. While the examples of the disclosed subject matter will be discussed in relation to OSA, it will be appreciated that the features of the disclosed subject matter can be applied to surgical implant for nerve modulation for other conditions in mammalian bodies, mutatis mutandis. It will be further appreciated, that the presently disclosed subject matter is directed to the surgical implant, and the implant can be activated by an activator unit provided with a power source either applied externally or implanted in the body of the subject. In one example, the external activation unit for the implant is disclosed in other applications and patents to the applicant, disclosures of which are incorporated herein by reference.

FIGS. 1A to 1E and FIG. 2 illustrate an example of the surgical implant in accordance with the disclosed subject matter. The implant may be formed of any materials suitable for implantation into the body of a patient. The implant in accordance with the disclosed subject matter is at least partially encapsulated in a biocompatible material. The implant may be substantially encapsulated at least in one layer of a biocompatible polymer including at least one of silicone, phenyltrimethoxysilane (PTMS), polymethyl methacrylate (PMMA), parylene C, polyimide, liquid polyimide, laminated polyimide, epoxy, polyether ether ketone (PEEK), liquid crystal polymer (LCP), KAPTON, or combinations thereof. In addition, the implant may be encapsulated at least in one layer of a biocompatible polymer, and include one or more additional layer covering portions thereof. It will be appreciated that the implant may include ceramic material, thermoplastic material such as ULTEM, or other compatible materials.

The surgical implant, generally designated 100, comprises a substantially planar central body portion 120 having a top side 122 and a bottom side 124; two adjustable wing portions 132A and 132B; connecting members 134A and 134B (in the illustrated example, each connecting member comprising two elements 136A and 136B as will be further described hereinafter). The connecting members extending respectively from opposite sides of the central body portion 120, each of the connecting members is configured for flexibly connecting each one of the two wing portions 132A and 132B to said central body portion 120 at opposite sides thereof.

Figure 3:
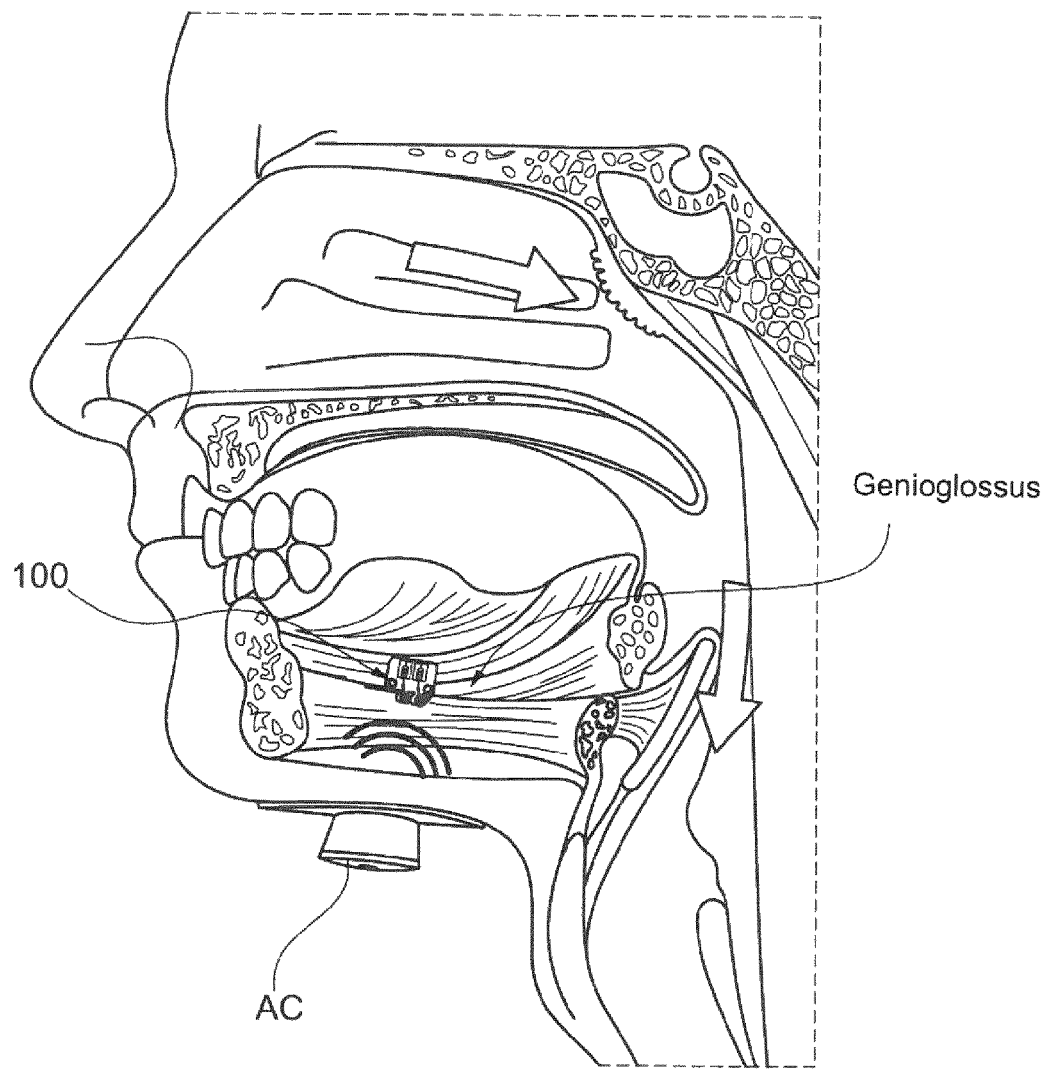
FIG. 3 illustrates the surgical implant in accordance with the disclosed subject matter, e.g. of FIG. 1, positioned over the genioglossus muscle.

While the description provides for the structural features of the disclosed surgical implant, in accordance with the disclosed subject matter the implant further comprises electronic components configured to stimulate a nerve when implanted in a subject in a location that permits it to modulate a nerve (e.g. as seen in FIG. 3) as will be discussed, without being in a direct contact with the nerve to be modulated/stimulated. When used to stimulate a nerve for the treatment of obstructive sleep apnea, the implant unit 100 may be placed on a genioglossus muscle so as to neuromodulate a hypoglossal nerve, which at least partially may extend within the muscle. In one example, due to the structure of the surgical implant, its flexibility and the degrees of freedom of the connecting members and the wing portions, it allows for neuromodulation of nerve branches otherwise not accessible as these are either extending within the muscle tissue or are branched out such that only emitting of electrical filed over an area covering the respective branches of the nerve will permit neuromodulating of the nerve, such as the terminal branches of the hypoglossal nerve.

For example, implant may include an antenna a (seen e.g. in FIGS. 1A and 2) and associated electronic circuit and components mounted onto or integrated with central body portion (160, details not shown). The antenna a may include any suitable antenna known to those skilled in the art that may be configured to send and/or receive signals and power. The antenna may include any suitable size, shape, and/or configuration accommodated by the dimensions of the implant. The size, shape and/or configuration may be determined by the patient anatomy, the placement location of the implant unit, the amount of energy required to neuromodulate the nerve, etc. Suitable antennas may include, but are not limited to, a long-wire antenna, a patch antenna, a helical antenna, PCB antenna, etc.

Figure 1B:
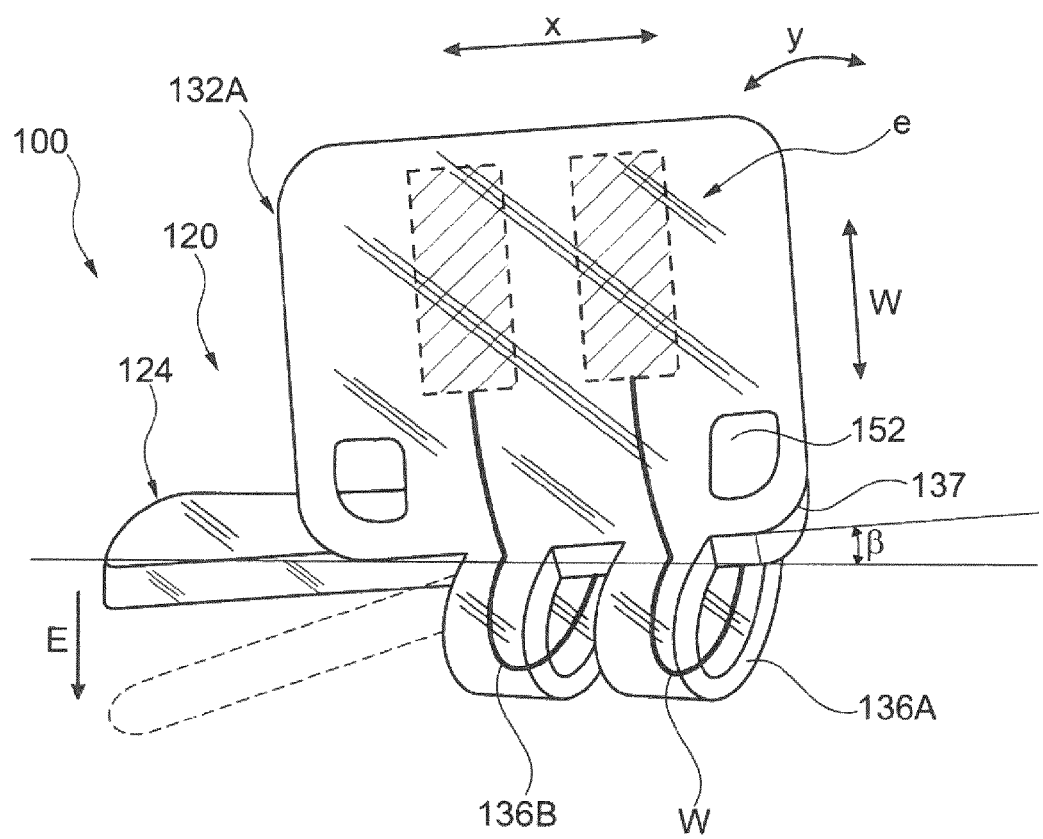
FIG. 1B is a side view of the surgical implant of FIG. 1A.
Figure 2:
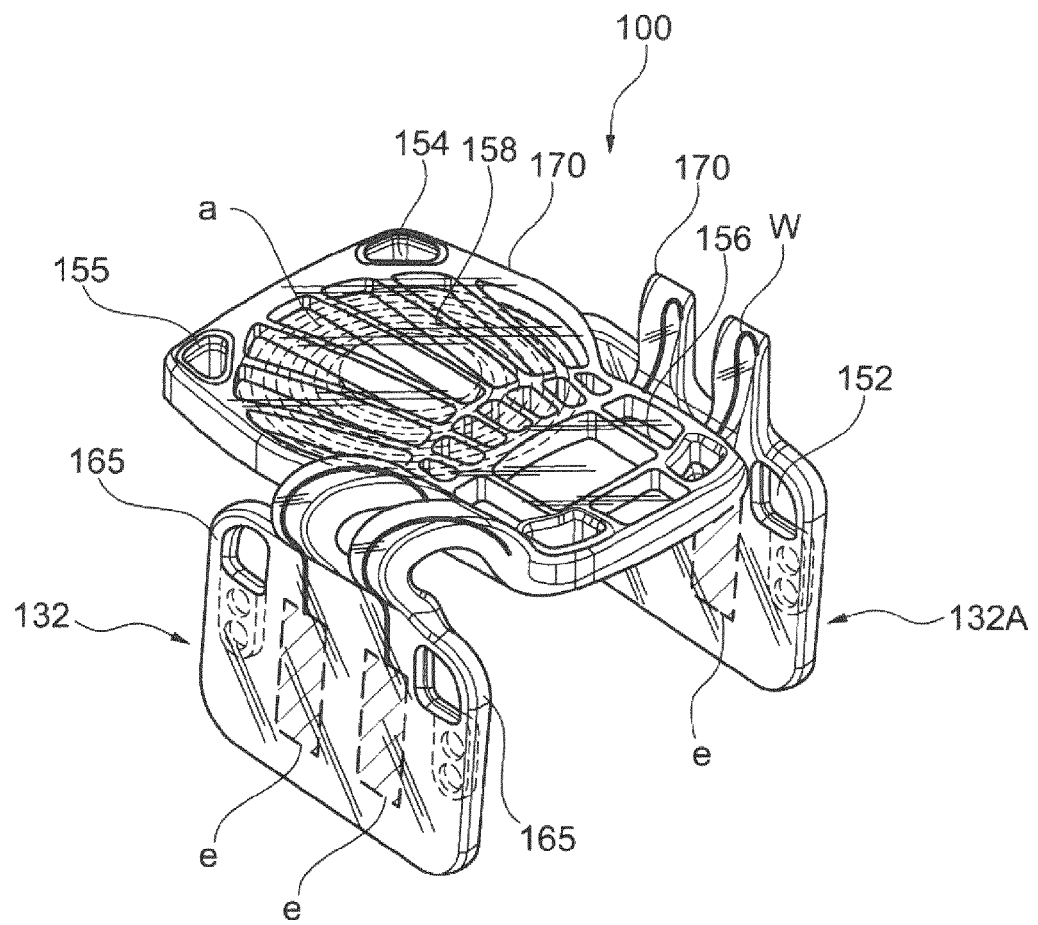
FIG. 2 is another perspective view of the surgical implant in accordance with an example of the disclosed subject matter, showing substantially transparent outer surface.

Implant may additionally include a plurality of field-generating implant electrodes generally designated e (e.g. FIG. 1A, 1B, 2). The electrodes e may include any suitable shape and/or orientation on the implant unit so long as the electrodes may be configured to generate an electric field in the body of a patient. Implant electrodes may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, circular electrodes, and/or circular pairs of electrodes. As shown in FIG. 1B, electrodes e may be located on the wing portions connected by connecting wires W to the electronic components and the antenna on the central body portion.

The electrodes e, however, may be located on any portion of wing portions. The connecting wires are configured to extend through the connecting members and are sized and shaped to be encapsulated therein. In accordance with an example, the wires W extend in designated channels. In accordance with yet an example, the wires may extend in designated reinforced channels. In accordance with some examples, the connecting members are provided with designated channels (not shown) configured to retain the connecting wires in place and further facilitating the flexibility of the connecting members without braking or damaging the wires and their respective connections to the components on the central body portion and the respective electrode. The implant may further include circuit components 160 and any other required components facilitating the antenna to receive the energy and transmitting this energy for the electrodes to emit the electric filed to the nerves. In the illustrated example, the implant does not comprise a power source. The implant in the illustrated example is activated externally. It will be appreciated that other means of activating the implant can be envisioned, either externally or internally. The implant unit can be activate using wifi, RF, IR or Bluetooth technologies.

Implant electrodes e may be spaced apart by about a distance of about 0.2 mm to 40 mm. In other embodiments, the electrodes may be spaced apart by a distance of approximately up to 12 mm. In accordance with yet an example, the distance may be approximately 0.5-7 mm measured between the internal edges of the electrodes. To protect the antenna, electrodes, circuit components, and connecting wires from the environment within a patient's body, implant may include a protective coating that encapsulates the implant 170. In some embodiments, the protective coating may be made from a flexible material to enable bending thereof, such as silicone. The encapsulation material of the protective coating may also resist humidity penetration and protect against corrosion. The surgical implant is substantially sealed and impervious to fluid. The term "substantially sealed implant" as used herein refers to the condition of having a sufficiently low unintended leakage and permeation rate under given fluid flow or pressure conditions. It will be appreciated that the first pair of electrodes and the second pair of electrodes may be partially covered at their periphery with the encapsulating material, having at least a portion thereof exposed however sealing the implant such that no fluid will enter or exit through the seal surrounding the open window of the electrodes. For example, the first pair of electrodes and the second pair of electrodes are partially embedded within the encapsulating material and comprise an outer layer of encapsulating material extending thereover and leaving at least a portion thereof exposed to the environment.

Figure 1C:
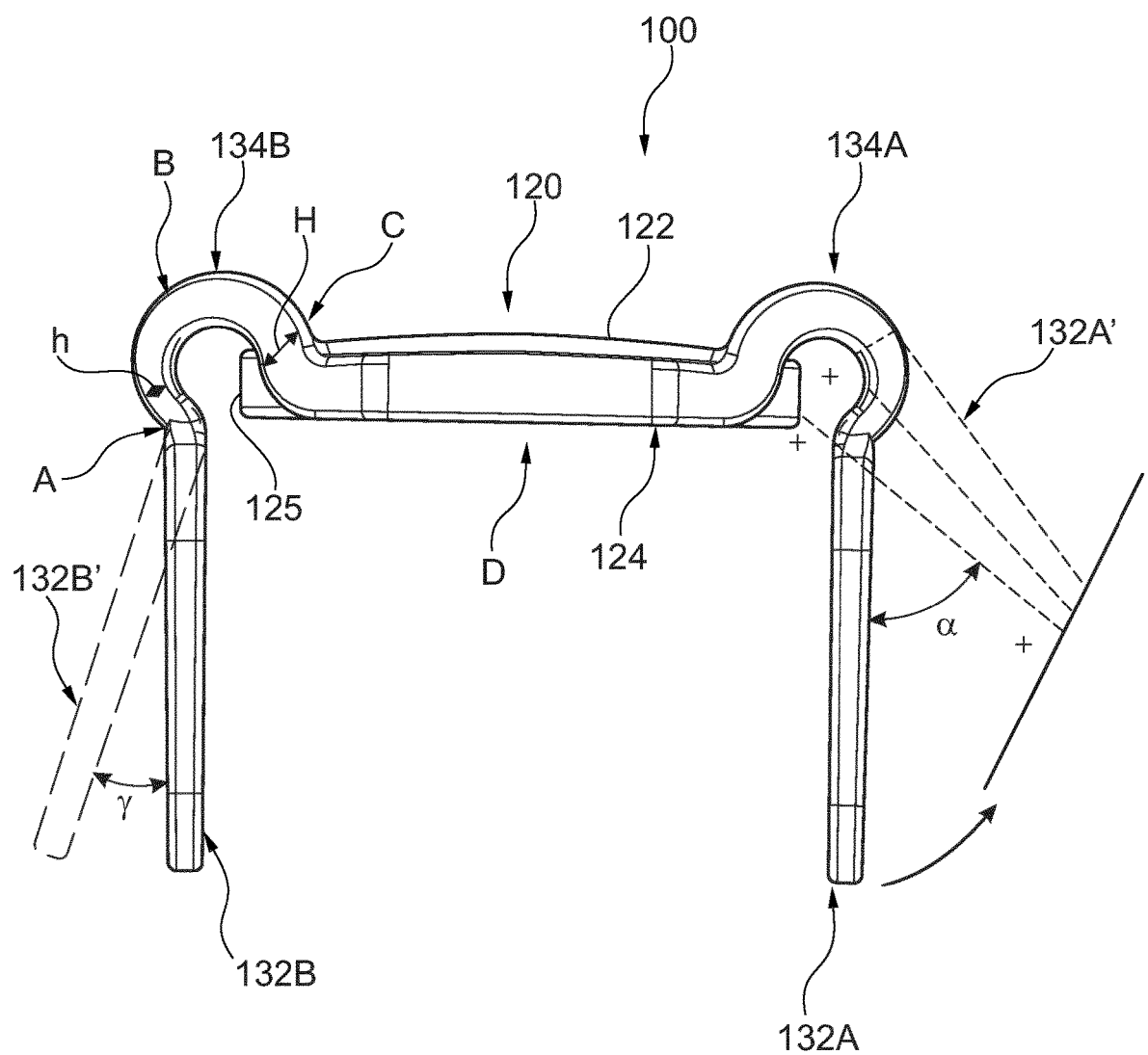
FIG. 1C is a front view of the surgical implant of FIG. 1C.

As seen in FIG. 1A, each one of the two connecting members is constituted by two parallelly extending arched elongated elements 136A and 136B, each extending at an angle and hingedly from the central body 120, such that the connecting members are integrally formed with and extend from the central body portion, allowing for at least one degree of freedom, as will be discussed. Such a connecting may be through a hinge which may be a living hinge, integral hinge, segmented hinge, etc. The arched elongated segments extend from the side edge 125 and project above the top side 122 of the central body portion 120, as best seen in FIG. 1C, with the wing portions 132A and 132B, each integrally formed with and extending from the opposite ends of the elongated segments. These elongated segments in accordance with the example, house the connecting wires W extending from the components contained in the central body portion to the respective electrodes e disposed on the wing portions 132A and 132B, the wires are provided in a configuration that will allow their deformation without disconnection from the main body or the electrodes. For examples the wire may be in excess, e.g. undulation, coiled etc. It will be appreciated, that while in the exemplified implant 100, each connecting member comprises two separate segments, in accordance with the disclosed subject matter, the connecting member may be a single segment. In accordance with another example, the two separate members may be connected with a connecting layer therebetween, either continuously, leaving no opening between the arched elongated segments, or with a non-continuous, layer, interconnecting the segments.

As further seen in FIG. 1C, each one of the two wing portions is integrally articulated to the respective elongated segments (extension members) extending between the central body portion and the two wing portions.

The connecting member may be a flexible element configured to deform in at least one direction. The connecting member can be of a unitary thickness or as exemplified and best seen in FIG. 1C of thickness decreasing from the portion closest to the area of connection with the central body designated H to thickness designated h at the portion closer to the wing portions. The decrease in thickness can be gradual (as shown) or alternatively provided in segments. Such decrease in thickness provides for flexibility of the connecting members and allows for degrees of freedom both to the connecting members and the movement of the wing portions. The connecting members are configured to endure strain, particularly due to being bent, folded, or stretched, without breaking or suffering permanent injury. "Flexible" as used herein may or may not include the further properties of being resilient or elastic. Deformation could refer to at least one parameter change, e.g. change of length, thickness etc. in a pre-specified space.

The connecting members allow several degrees of freedom to the two wing portions as best illustrated in FIGS. 1B and 1C. The connecting members are configured with flexibility along the length thereof and at least at points designated C, B and A, where point C designates the section at the connection of the elongated segment to the central body portion, point B designates the segment at around the center of the arch of the elongated member and point A designates the segment integrally connecting the elongated members to the wing portions. Thus as seen in FIG. 1C at point B the elongated segment is allowed to deform and open the arch and move the wing portion at an angle $\alpha$ which can be between 0 degrees and up to 180 degrees. In other examples, the angle $\alpha$ can extend between −90 (e.g. in a direction towards the bottom side 124) to 270 degrees, or as shown at about 30 degrees. The wing portion can pivot at point A at angle $\delta$ which can be between 0 degrees to about 100 degrees. In other examples, the angle can extend between −90 (e.g. towards the bottom side 124) to 100 degrees, or as illustrated up to 25 degrees. It will be appreciated that while the angular displacement has been shown separately for each of the points a combination of displacement is allowed and the wing portions can be angled in combination with the angular or other deformation of the connecting members. In accordance with disclosed subject matter and illustrated example, 0 degrees is the resting position of the element which has the degree of freedom to change position(s).

As further seen in FIG. 1B, the wing portions can be displaced in the direction of arrow X (e.g. horizontally), arrow Z (vertically) or arrow Y (angularly, e.g. inwards the central portion or outwardly therefrom, where the wing portions can flex towards or away from each other). Such flexibility along multitude of dimensions, allow positioning of the implant and in particular its wing portions over the treated muscle, in a saddle like position and conform to the dimensions of the muscle, which may be different from subject to subject. The disposition of the wing portion is further defined by angle $\beta$ which provide for an angle between the edge 137 of the wing and the horizontal plane extending through the central body portion. The angle $\beta$ can be between about 0 degrees to 10 degrees, and in the illustrated example is between 3 to 7 degrees.

As already discussed, the surgical implant may be formed from a unitary elastomeric material. To allow anchoring of the implant in its designated position the implant may be provided with anchoring arrangements. In the disclosed example, the anchoring arrangement is in the form of suturing holes (e.g. 152, 155). As the implant is made of an elastomeric material, to reinforce the suturing holes, the implant may be provided with anchoring elements made of a material configured to withstand the forces acting on the implant and the sutures, e.g. during the tongue movement. Such a material can be e.g. a PEEK, ceramic, titanium etc.

Figure 1D:
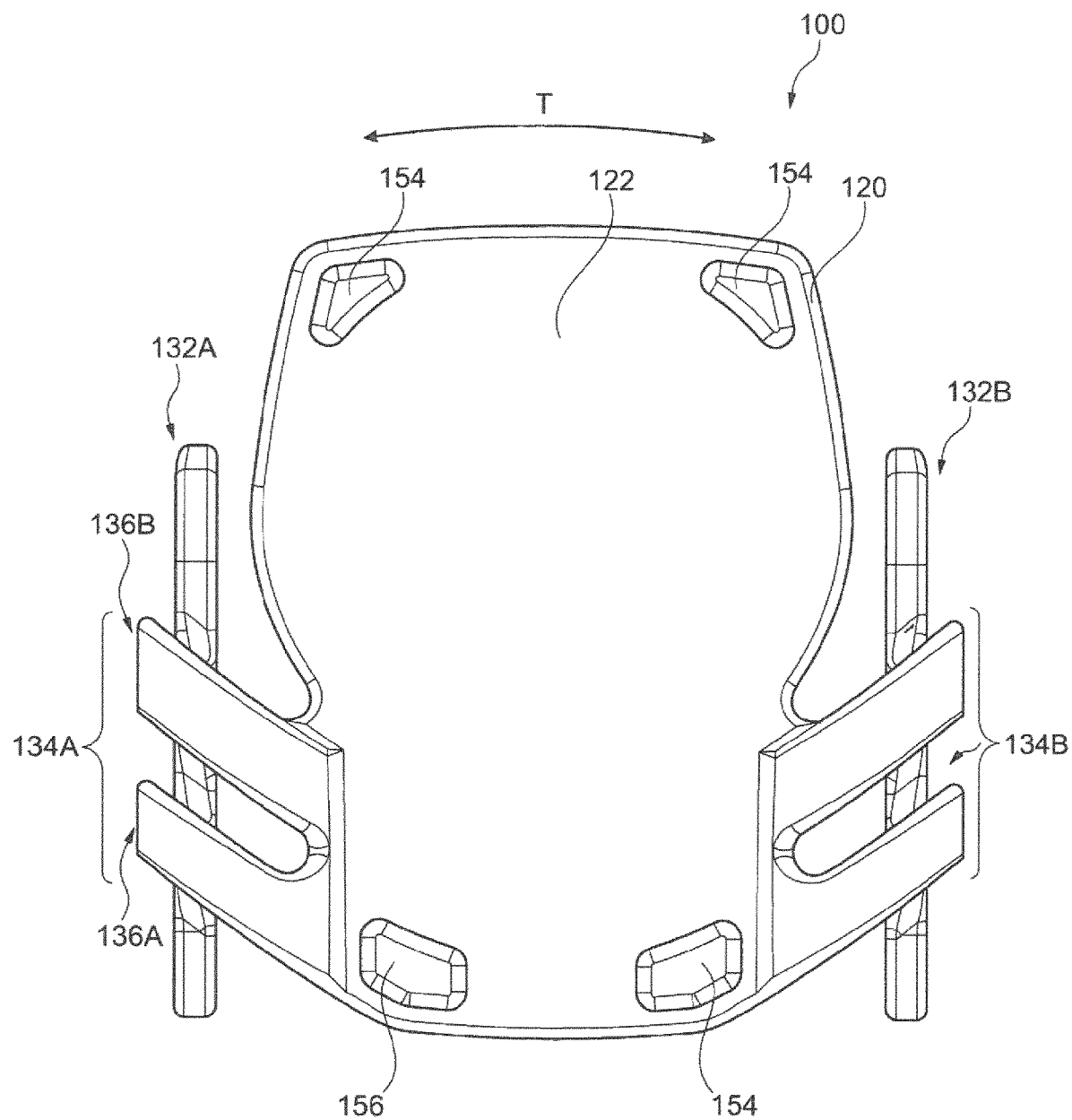
FIGS. 1D and 1E are a top and bottom plan view of the surgical implant of FIG. 1A, showing the outer contour lines thereof.
Figure 1E:
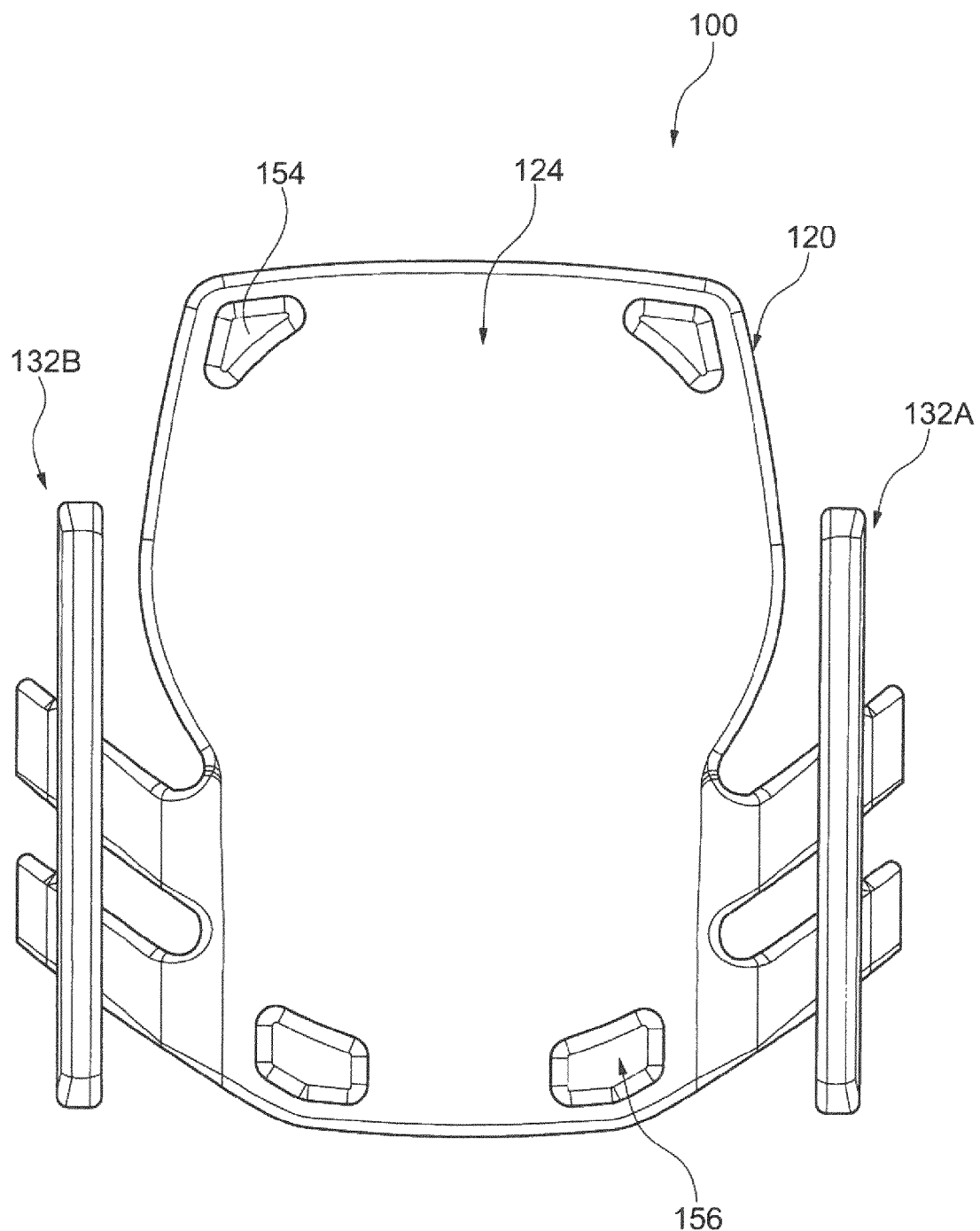

As seen in FIG. 1B the suturing holes 152 can be provided at the wing portions at the desired location. In addition, other anchoring elements can be provided at the central body portion, e.g. adjacent the edges thereof as seen in FIG. 1D designated as 154. It will be appreciated that other configurations for anchoring the implant are envisioned and while for example the central body portion comprises four such holes, only few or none of these can be provided. In addition, the positioning of the suture holes on the wing portions as illustrated in the accompanying drawings are for illustration purposes only and other shapes, configurations and positions thereof are envisioned. Other types of anchoring arrangements are envisioned, such as adhesives, staples etc, as disclosed herein.

The central body portion can further be provided with a load bearing reinforcing structure 158, internally disposed, and configured to provide structural rigidity to the central body portion. The reinforcing structure can be resilient and allow for a degree of flexibility to the central body portion when force is applied thereto in the direction of arrow E, allowing at least a portion of the central body portion to flex e.g. as seen in FIG. 1B, the reinforcing structure in the illustrated example is provided through the central body and provides for a walled structured 156 to surround the electronics 160 and also longitudinal ribs 158 as seen e.g. in FIG. 1A. It will be appreciated the reinforcing structure may have a different structure, e.g. crossed ribs to form a net like structure, a spiral, e.g. interconnected stips, etc. to provide for the same function of reinforcement and substantial exposure of the antenna a and the electronic parts.

The implant may further comprise a surgical mesh, e.g. polymeric mesh, provided at least over a portion thereof. In another example, the surgical mesh may be of any suitable material.

In another aspect of the disclosed subject matter there is disclosed an implant unit activation device illustrated in FIGS. 4 to 7C and generally designated 200. The device, comprises a main body 220 comprising an implant activator and an axially displaceable retractor 240 configured to displace relative the main body.

Figure 6:
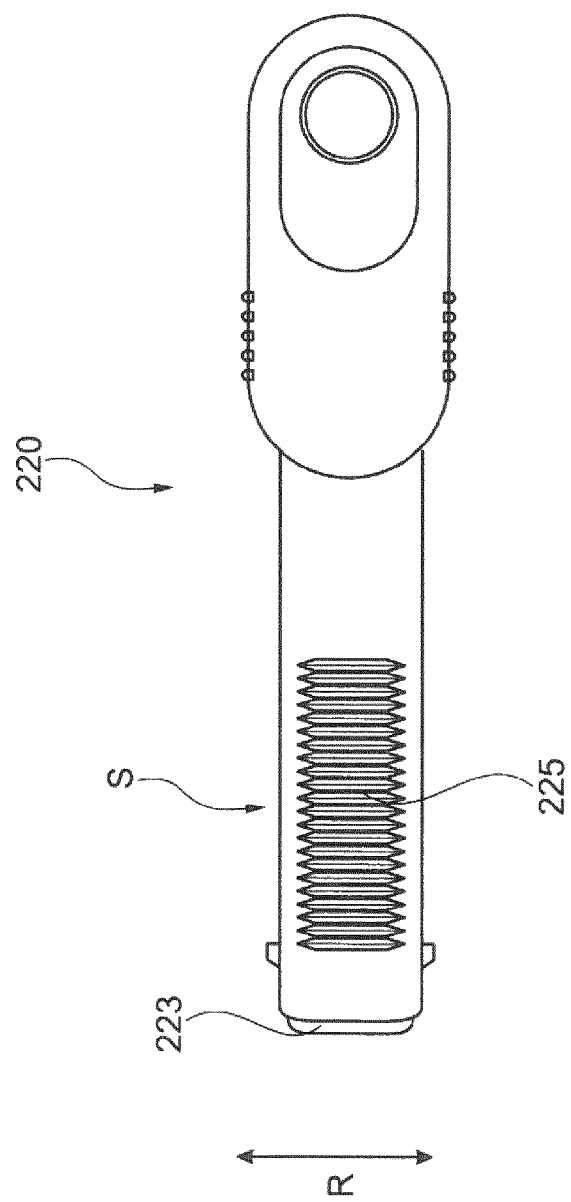
FIG. 6 is a top view of the main body of the implant activator of FIG. 4.
Figure 7A:
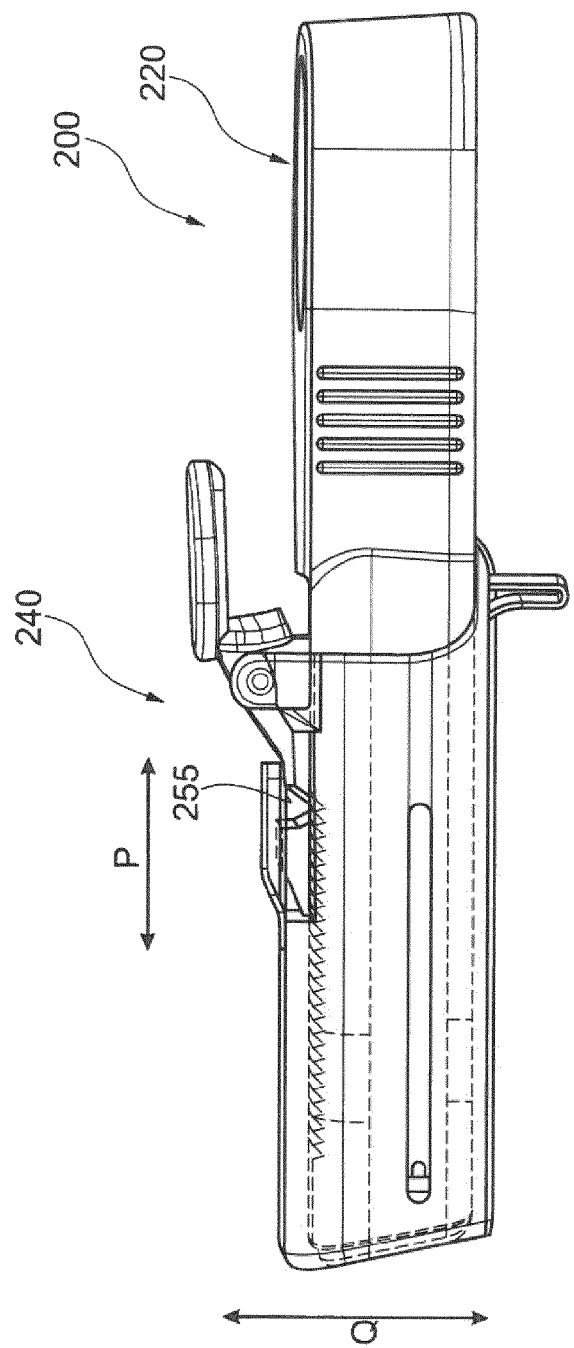
FIG. 7A and FIG. 7B (partially) illustrate the implant activation device of FIG. 4, with the adaptor in a semi-transparent view.
Figure 7B:
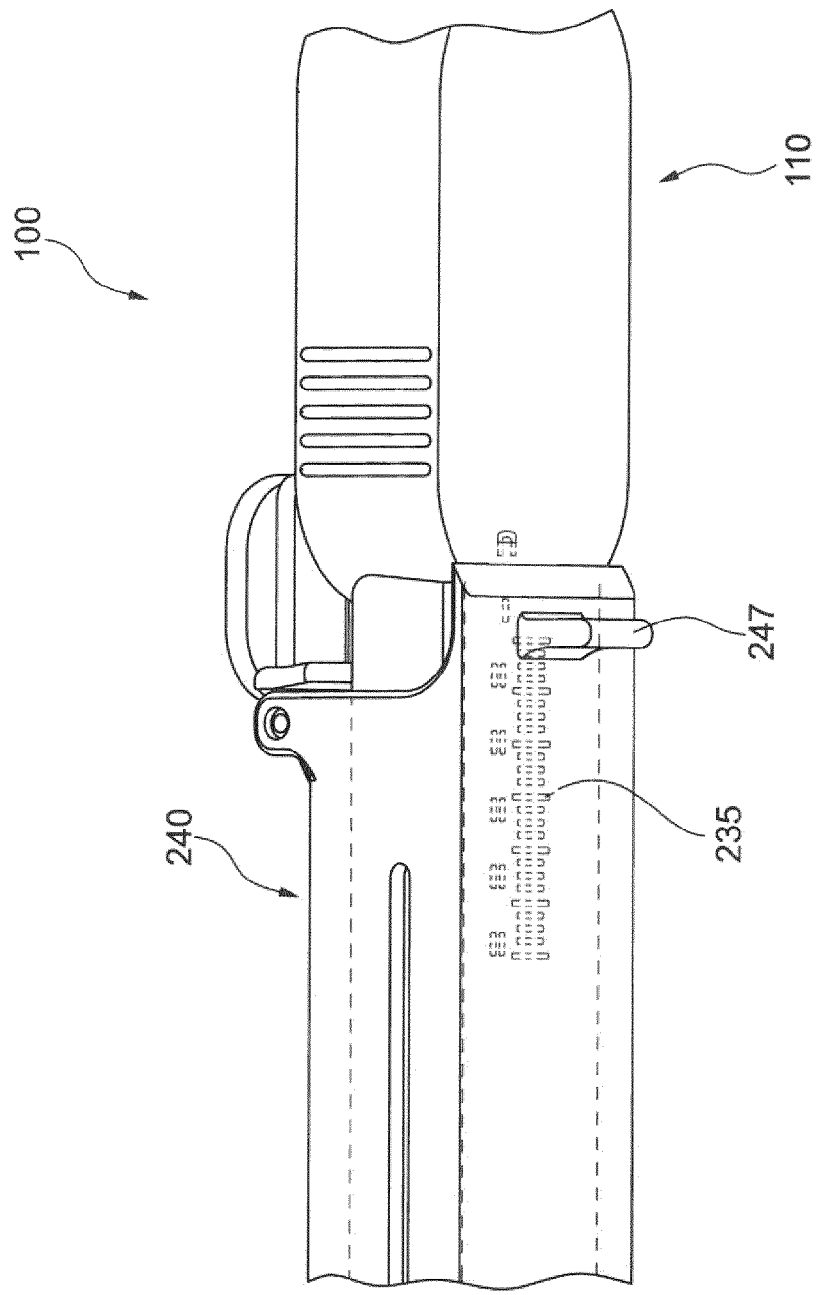
Figure 7C:
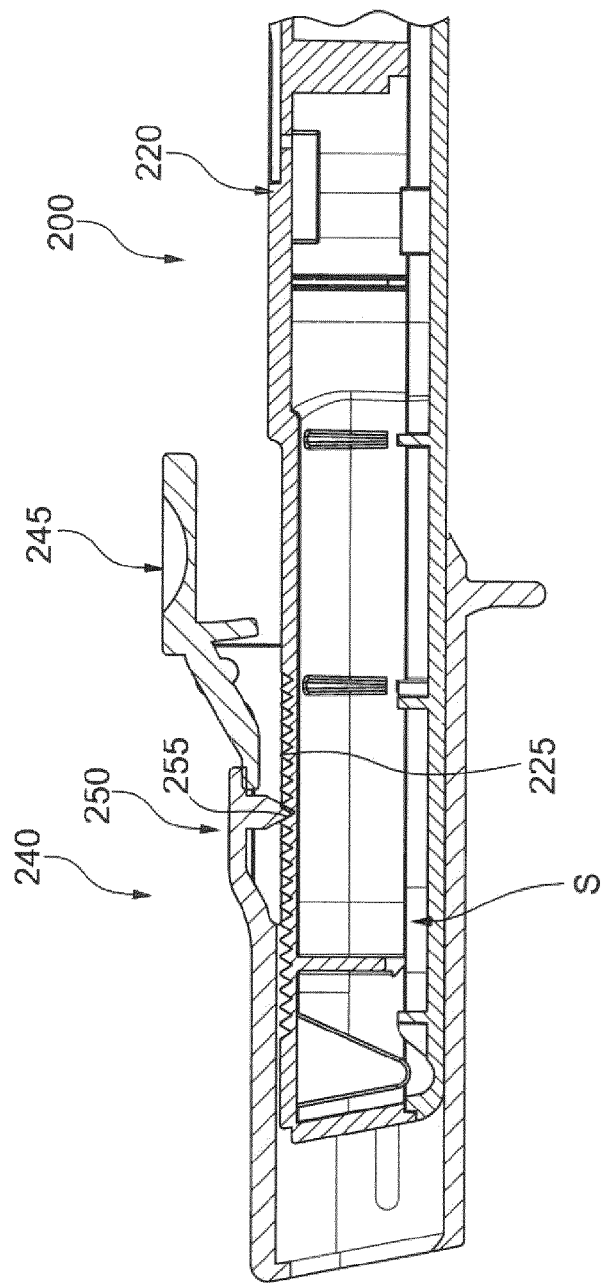
FIG. 7C illustrates the implant unit activation device in a cross section along line A-A in FIG. 4.

The implant activator comprises an antenna, a power source and associated circuitry (not shown) and being configured to wirelessly transfer energy from the power source to an implant unit (e.g. surgical implant 100) during implantation of the implant unit into the body of a subject to cause stimulation of at least one nerve in the body of the subject during the implantation procedure. The axial displacement of the retractor 240 allows adjusting of the degree of energy received by the implant unit. The activation device is configured to deliver energy to the implant unit with the retractor allowing to displace or more particularly retract the activation unit in the direction of arrow P (seen in FIG. 7A) from the implant so as to control the amount of energy received by the implant unit as a function of distance at which it is delivered thereto. As an alternative example, the axis of displacement may comprise e.g. displacement along axis Q and\or R (e.g. as shown in FIGS. 6 and 7A).

Figure 4:
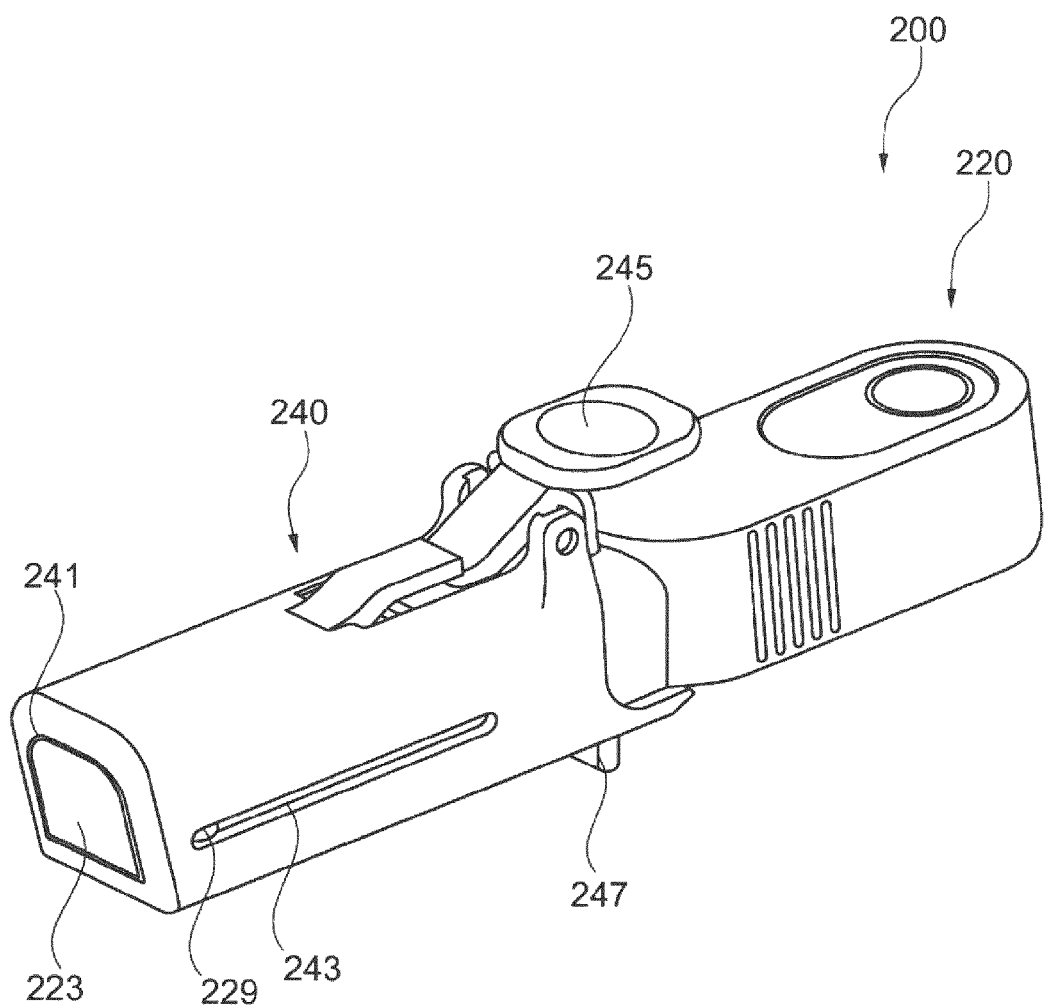
FIG. 4 is a perspective side view of the implant unit activation device in accordance with one example of the disclosed subject matter.
Figure 5:
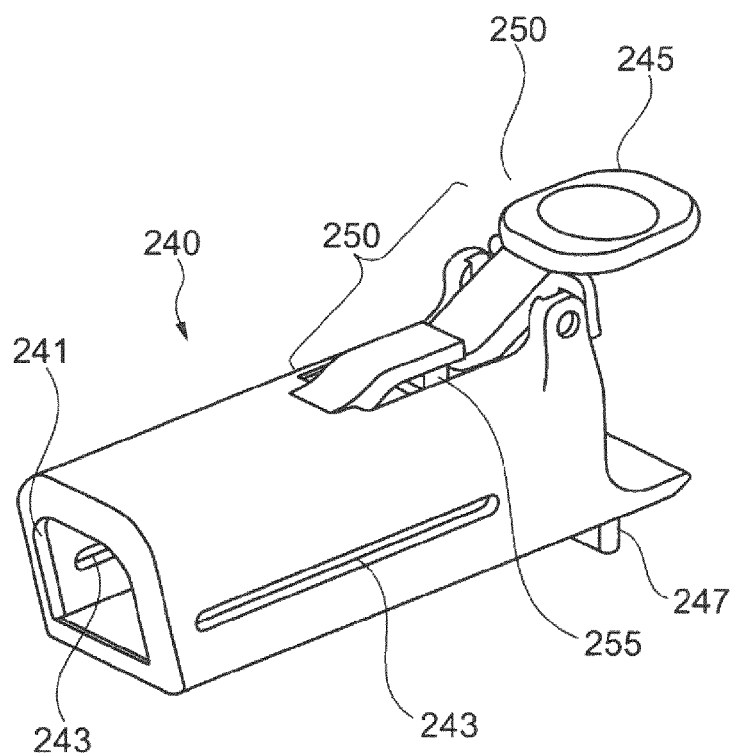
FIG. 5 is a perspective side view of the axially displaceable adaptor of FIG. 4.

The retractor 240 is in this example a sleeve like member configured to controllably slide over the main shaft S of the activation device main body. The sleeve like member defines a hollowed and axially extending interior which securably mounts over the shaft of the main body. To facilitate the retraction, the sleeve like member is provided with a release lever 245 and engagement mechanism 250, such that the engagement mechanism is configured to selectively engage the corresponding engaging members 225 on the shaft of the main body. In the present example the shaft is provided with toothed surface 225 and the inner side of the sleeve is provided with the engagement mechanism 255 constituted by a protrusion configured to engage the toothed surface to lock thereagainst. The main body shaft may be provided with indicia 235 allowing the user to determine the location at which it is desired to lock the sleeve against the shaft. As seen in FIG. 4, the shaft is provided with a protrusion 229 which when aligned with the sleeve extends slidable in a slit 243 in the sleeve which in the example extends at two opposite sides of the sleeve as seen in FIG. 5. It will be appreciated that other configurations are envisioned that will allow the main body of the activation device to be distanced from the implant unit keeping the device at the predetermined position with respect to the implant unit. The sleeve can further be provided with a support and gripping element 247 to allow the user to grip the sleeve, while activating the lever 245 to release the engagement of the mechanism 255 and retracting the shaft body through the sleeve to distance its end portion 223 from the opening 241 in the sleeve.

As seen in the illustrated example, the edge of the device 200 is angled to enable line of sight during use and for ergonomic considerations. It will be appreciated, that while in the illustrated example the amount of energy or power level is determined by the axial movement of the retractor, other examples include a screw on sleeve, partial elements extending from the shaft and configured to distance the edge of the shaft from the point of contact with the implant device. In an alternative example, the amount and level of energy may be controlled directly through the device, without adjusting the distance between the shaft edge relative the implant device.

An exemplary method of positioning and activating a neurostimulation implant device (e.g. surgical implant 100) in accordance with the disclosed subject matter is provided. The method in accordance with the disclosed subject matter, comprises:

providing the implant and positioning it over the tissue of the subject, e.g. the genioglossus muscle.

Providing an implant unit activation device as disclosed, the device comprising: a main body comprising an implant activator having a power source, a second antenna configured to provide a signal to the first antenna and an axially displaceable adaptor\retractor associated with the implant activator, the implant activator configured to wirelessly transfer energy from a power source to the implant during implantation to cause modulation of at least one nerve in the body of the subject; and wherein the axial displacement (e.g. retraction) of the adaptor from at least a first position to at least a second position allows adjusting of the degree of energy received by the implant unit.

To determine the correct location for positioning the implant and in particular the electrodes to stimulate the nerve, next stem comprises identifying the stimulation threshold by determining a degree of nerve modulation response for each of the at least first pair of electrodes and a second pair of electrodes by positioning said first pair of electrodes at an estimated implant location proximal to the nerve and selectively displacing the second antenna to deliver a first amount of power and a second amount of power required to obtain a stimulation threshold in at least the first pair of electrodes based on one or more patient signals;

positioning the at least the second pair of electrodes at an estimated location and delivering the second amount of power required and determining a degree of nerve modulation by the at least said second pair of electrodes.

wherein the stimulation threshold is based, at least in part on at least one neuromuscular response during stimulation of each electrode of the at least a first pair of electrodes and a second pair of electrodes.

In one embodiment the implant may be configured for treatment of obstructive sleep apnea and the location of implantation may be in the vicinity of the hypoglossal nerve. In accordance with this embodiment the neurostimulation device may be configured to modulate at least one branch of the hypoglossal nerves.

The second amount may be greater or equal to the first amount of power.

The second amount may be equal to or less relative the first amount of power.

The invention claimed is:

1. A surgical implant, comprising:
a substantially planar central body portion having a top side and a bottom side;
at least two adjustable wing portions;
at least two connecting members, each of the at least two connecting members extending from opposite sides of the substantially planar central body portion, each of the at least two connecting members configured for flexibly connecting each of the at least two adjustable wing portions at opposite sides to the substantially planar central body portion; and a plurality of electrodes, one or more of the plurality of electrodes located on each of the at least two adjustable wing portions;

wherein the surgical implant is sized and dimensioned to be positioned on and conform to an exterior surface of a muscle with the at least two wing portions positioned at sides of the muscle when implanted into a subject; and wherein the substantially planar central body portion, the at least two adjustable wing portions, and the at least two connecting members exhibit single piece construction.

2. The surgical implant of claim 1, wherein each of the at least two connecting members extend from the substantially planar central body through at least one hinge member.

3. The surgical implant of claim 2, wherein each of the at least two adjustable wing portions is hingedly articulated to the at least two connecting members.

4. The surgical implant of claim 1, wherein the at least two adjustable wing portions are more flexible than the substantially planar central body portion.

5. The surgical implant of claim 1, wherein each of the at least two connecting members is flexibly connected to each of the at least two adjustable wing portions via a hinge and, wherein the hinge is thinner than an adjacent portion of the at least two adjustable wing portions.

6. The surgical implant of claim 1, wherein each of the at least two connecting members is flexibly connected to each of the at least two adjustable wing portions via a flexible element configured to deform in at least one direction.

7. The surgical implant of claim 1, wherein each of the at least two connecting members is flexibly connected to each of the at least two adjustable wing portions via a flexible arch permitting bending movement along a length thereof in a first direction such that the substantially planar central body and each of the at least two adjustable wing portions flex away from each other.

8. The surgical implant of claim 1, further comprising a flexible arch, wherein the flexible arch includes:

at least one central segment arranged along a length of the flexible arch; and at least two hinge structures, each of the at least two hinge structures disposed between the substantially planar central body and the at least one central segment and one of the at least two adjustable wing portions and the at least one central segment and oriented in a direction transverse to a length of the at least one central segment.

9. The surgical implant of claim 8, wherein the flexible arch is formed from a single elastomeric material, and wherein the at least two hinge structures include living hinges.

10. The surgical implant of claim 8, wherein the flexible arch is formed from multiple segments, and wherein the multiple segments are connected through living hinges.

11. The surgical implant of claim 8, wherein the flexible arch has a narrowing width with a largest width at an area of connection to the substantially planar central body and a narrower width at an area of connection with at least one of the at least two adjustable wing portions.

12. The surgical implant of claim 1, wherein the surgical implant is formed from a single elastomeric material.

13. The surgical implant of claim 1, further comprising at least one anchoring arrangement.

14. The surgical implant of claim 13, wherein the at least one anchoring arrangement is in a form of at least one suture hole.

15. The surgical implant of claim 14, wherein the at least one suture hole is provided on the substantially planar central body portion and/or at least one of the at least two adjustable wing portions.

16. The surgical implant of claim 1, further comprising an antenna secured to the central body portion and the one or more electrodes on each of the at least two adjustable wing portions in electric communication with the antenna.

17. The surgical implant of claim 16, wherein the one or more electrodes on each of the at least two adjustable wing portions are configured to receive an electrical current and emit an electrical field responsive to a signal received by the antenna.

18. The surgical implant of claim 1, wherein the surgical implant is positionable in a saddle-like configuration with the central body portion between the at least two adjustable wing portions and the at least two connecting members each forming a living hinging having a flexible arch configuration.

19. The surgical implant of claim 1, wherein the muscle is a genioglossus muscle.

* * * * *